US006200781B1

(12) United States Patent
Tal et al.

(10) Patent No.: US 6,200,781 B1
(45) Date of Patent: Mar. 13, 2001

(54) APPARATUS, SYSTEM AND METHOD FOR AUTOMATED EXECUTION AND ANALYSIS OF BIOLOGICAL AND CHEMICAL REACTIONS

(75) Inventors: Michael Tal, Kfar Bilu; Yoram Liran, Rehovot; Zvi Koren, Kiriat Bialik, all of (IL)

(73) Assignee: Integrated Genetic Devices, Ltd., Rehovot (IL)

( * ) Notice: Subject to any disclaimer, the term of this patent is extended or adjusted under 35 U.S.C. 154(b) by 0 days.

(21) Appl. No.: 09/339,865

(22) Filed: Jun. 25, 1999

(51) Int. Cl.[7] ............................ C12P 19/34; C12Q 1/68; C12M 1/34; B32B 27/04

(52) U.S. Cl. ............................ 435/91.1; 435/91.1; 435/6; 435/287.2; 422/131

(58) Field of Search ............................ 435/6, 91.2, 287.2; 422/131

(56) References Cited

U.S. PATENT DOCUMENTS

| | | | |
|---|---|---|---|
| 4,683,195 | 7/1987 | Mullis et al. . | |
| 4,683,202 | 7/1987 | Mullis . | |
| 5,843,650 | 12/1998 | Segev . | |
| 5,846,709 | 12/1998 | Segev . | |
| 5,897,842 | 4/1999 | Dunn et al. . | |
| 5,922,591 * | 7/1999 | Anderson et al. ................ | 435/287.2 |

* cited by examiner

*Primary Examiner*—John S. Brusca
*Assistant Examiner*—Jeffrey S. Lundgren

(57) ABSTRACT

An apparatus for controlling the temperature of at least one liquid reaction mixture, the apparatus including (a) at least one reaction vessel having open proximal and distal ends, the at least one reaction vessel including a gas permeable, liquid retaining, barrier positioned at a proximal portion thereof; (b) a pump being in fluid communication with the proximal end of the at least one reaction vessel through the barrier, for generating negative or positive pressure within the at least one reaction vessel, for translocating the at least one liquid reaction mixture through the distal end into and out of the at least one reaction vessel; and (c) a temperature controller being in thermal communication with the at least one reaction vessel for controlling the temperature of the at least one liquid reaction mixture when maintained within the at least one reaction vessel.

24 Claims, 8 Drawing Sheets

```
                    SEQUENCE LISTING


(1) GENERAL INFORMATION:

   (iii) NUMBER OF SEQUENCES:        2


(2) INFORMATION FOR SEQ ID NO:1:

     (i) SEQUENCE CHARACTERISTICS:
          (A) LENGTH:22
          (B) TYPE:nucleic acid
```

-continued

```
        (C) STRANDEDNESS:single
        (D) TOPOLOGY:linear

   (xi) SEQUENCE DESCRIPTION: SEQ ID NO:1:

GTAATACGAC TCACTATAGG GC                                    22


(2) INFORMATION FOR SEQ ID NO:2:

    (i) SEQUENCE CHARACTERISTICS:
        (A) LENGTH:30
        (B) TYPE:nucleic acid
        (C) STRANDEDNESS:single
        (D) TOPOLOGY:linear

   (xi) SEQUENCE DESCRIPTION: SEQ ID NO:2:

CTAGCTAGCA GTGAAATTGA CCGATCAGAG                            30
```

APPARATUS, SYSTEM AND METHOD FOR AUTOMATED EXECUTION AND ANALYSIS OF BIOLOGICAL AND CHEMICAL REACTIONS

FIELD AND BACKGROUND OF THE INVENTION

The present invention relates to an apparatus, system and method for executing and analyzing biological and chemical reactions automatically. More particularly, the present invention relates to an apparatus, system and method for automating the execution of a nucleic acids reaction, such as, for example, the polymerase chain reaction (PCR) in an open sample tube, thus allowing the automated analysis thereof either during or immediately following the nucleic acid reaction.

Diagnostic and research biology and chemistry rely heavily on the ability to perform various biological and chemical reactions in vitro. Such reactions are typically accomplished under controlled conditions which, aside from appropriate sample preparation, typically include temperature and time modulation.

An excellent example to an in vitro biological reaction is the polymerase chain reaction (PCR). The methodology of the polymerase chain reaction is described in detail in U.S. Pat. Nos. 4,683,202 and 4,683,195 which are incorporated herein by reference.

PCR has proven to be a phenomenal tool for diagnostics and research in many scientific fields including, but not limited to, genetics, molecular biology, cellular biology, clinical chemistry, forensic science, and analytical biochemistry, see, for example, Erlich (ed.), 1989, PCR Technology, Stockton Press (New York); Erlich et al. (eds.), 1989, Polymerase Chain Reaction, Cold Spring Harbor Press Cold Spring Harbor, New York; Innis et al., 1990, PCR Protocols, Academic Press New York; and White et al., 1989, Trends in Genetics 5/6:185–189.

The use of PCR can replace a large fraction of molecular cloning and mutagenesis operations, commonly performed in bacteria, thus providing speed, simplicity and at the same time lowering costs. Furthermore, PCR permits the rapid and highly sensitive qualitative and even quantitative analysis of nucleic acid sequences, enabling non-radioactive associated detection, thus overcoming the risks and restrictions associated with the utilization of radioactive isotopes.

Additional reactions which are propagated by carefully controlling and cycling the reaction temperature, include, but are not limited to, chemical amplification of nucleic acid sequences, as for example described in U.S. Pat. Nos. 5,846,709 and 5,843,650, ligase chain reaction, nucleic acid sequencing and the like.

Although PCR provides numerous advantages in research, the use of thermal cycling on a large scale in clinical laboratories is not widespread. This is largely due to the fact that complex and cumbersome steps are required to prepare nucleic acid samples for analysis. Such steps when effected for a large number of samples, as is typical in diagnostics, are time consuming and may lead to the generation of errors and contamination and/or expose workers to possible infection when effected manually. Furthermore, since the products of such PCR reactions must be analyzed to yield diagnostic results, transfer of the samples to an analytic instrument or in turn, real time analysis must be effected in an automatic manner.

To overcome some of these limitations, the use of an automated sample preparation coupled to thermal cyclers for large scale PCR reactions is practiced.

For example, Beckman Instruments, Inc. (Fullerton, Calif.) provides the Biomek® 2000 automated pipetting apparatus, that can automate the sample preparation steps for PCR or DNA sequencing reactions in a 96 well microtiter plate using a group of eight pipetting tips. Trays containing reagents or samples are arranged for sequential liquid transfer functions.

Another pipette robot, the Qiagen BioRobot™ 9600 (Qiagen Inc., Chatsworth, Calif.) can prepare 96 bacterial minipreps in 2 hours. These robots all use a cooling plate to keep the reagents and samples at controlled temperatures (usually 4° C.) during sample preparation.

The reagent trays prepared in apparatuses of this type are then generally transferred typically automatically to a separate instrument for purposes of thermal cycling.

For example, the RoboCycler™ Gradient 96 System (Stratagene, Inc.) has 4 different temperature blocks and a lifter that moves a tray of up to 96 tubes from block to block in sequence. In this way, the apparatus cycles reaction mixtures through a series of preset temperatures as appropriate for amplification or sequencing reactions.

The Vistra™ DNA Labstation 625 (Molecular Dynamics, Sunnyvale, Calif.) is a pipette robot that can prepare bacterial mini-preps and PCR and DNA sequencing reactions in a 96 well microtiter plate. The Labstation 625 has an integrated Peltier-block thermocycler for thermal-cycling steps. Using this apparatus, a technician can prepare a sequencing experiment in about 10–15 minutes, and then start the thermocycling procedure. This apparatus uses tubes, and places a layer of oil on top of the reactions to reduce loss of sample during heating.

While there are many advantages to combining sample preparation and thermal cycling into a single apparatus, a further limitation which is not addressed by the above, is the automatic provision of the end products from PCR reaction to appropriate analysis devices, or alternatively analysis of these products during the course of the PCR reaction.

To partially overcome this problem, U.S. Pat. No. 5,897,842 describes an apparatus which automates the large number of pipetting steps and the thermocycling steps involved in preparing a nucleic acid sample while, at the same time, it is designed to automatically provide the resultant end products to analytic devices for further analysis.

Although the above mentioned apparatus provides major advantages over the above described art, it still suffers from several limitations.

To effect such automation the apparatus described in U.S. Pat. No. 5,897,842 utilizes flow-through reaction vessels, such as capillary tubes, for the preparation and thermal cycling of reaction mixtures. In order to prevent loss of the reaction mixture from the vessels during heating, the thermal cycling apparatus provides a formable seal for transiently sealing the distal end of each reaction vessel while positive pressure transiently seals the proximal end of the reaction vessel following the application of the formable seal to the distal end thereof.

As further described in the above patent, both generation of the positive pressure and sample drawing into the reaction vessels are effected by a single pump. Thus, to prevent cross contamination between the samples an appropriate fluid barrier, which can be provided within the proximal end of the reaction vessel must be utilized. Such a barrier is either described nor mentioned by U.S. Pat. No. 5,897,842, and as such, his apparatus is particularly prone to cross contamination of samples.

There is thus a widely recognized need for, and it would be highly advantageous to have, an apparatus and method for effecting automated nucleic acid reactions, such as PCR, while at the same time enabling analysis of the resultant products either during (real-time) or following the reaction, and yet be devoid of the above limitation.

SUMMARY OF THE INVENTION

According to one aspect of the present invention there is provided an apparatus for controlling the temperature of at least one liquid reaction mixture, the apparatus comprising (a) at least one reaction vessel having open proximal and distal ends, the at least one reaction vessel including a gas permeable, liquid retaining barrier positioned at a proximal portion thereof; (b) a pump being in fluid communication with the proximal end of the at least one reaction vessel through the barrier, for generating negative or positive pressure within the at least one reaction vessel, for translocating the at least one liquid reaction mixture through the distal end into and out of the at least one reaction vessel; and (c) a temperature controller being in thermal communication with the at least one reaction vessel for controlling the temperature of the at least one liquid reaction mixture when maintained within the at least one reaction vessel.

According to another aspect of the present invention there is provided a method of controlling the temperature of at least one liquid reaction mixture, the method comprising the steps of (a) providing at least one reaction vessel having open proximal and distal ends, the reaction vessel including a gas permeable, liquid retaining barrier positioned at a proximal portion thereof, (b) drawing the at least one liquid reaction mixture into the at least one reaction vessel from the distal end; (c) containing the at least one liquid reaction mixture within the at least one reaction vessel; and (d) setting a temperature of the at least one liquid reaction mixture contained within the at least one reaction vessel via a temperature controller.

According to further features in preferred embodiments of the invention described below, the at least one liquid reaction mixture is maintained within the at least one reaction vessel via the negative pressure generated therein.

According to still further features in the described preferred embodiments the apparatus further comprising a removable seal positionable at the distal end of the at least one reaction vessel, the removable seal being for restricting the at least one liquid reaction mixture within the at least one reaction vessel when scaled.

According to still further features in the described preferred embodiments the temperature controller is a thermocycler capable of cycling at least two temperature settings.

According to still further features in the described preferred embodiments the temperature controller includes a thermal block designed for accepting in intimate thermal contact the at least one reaction vessel.

According to still further features in the described preferred embodiments the thermal block forms a part of a thermocycler capable of cycling at least two temperature settings.

According to still further features in the described preferred embodiments the apparatus further comprising a housing for enclosing the at least one reaction vessel, wherein the temperature controller is an air-based thermal cycler, for providing a temperature controllable air stream into the housing.

According to still further features in the described preferred embodiments the at least one reaction vessel is of a material selected from the group consisting of glass, compound material, semiconductor material, plastic and metal.

According to still further features in the described preferred embodiments the at least one reaction vessel is composed of a heat conducting material.

According to still further features in the described preferred. embodiments the at least one reaction vessel is composed of an electricity conducting material.

According to still further features in the described preferred embodiments the at least one reaction vessel is removable from the apparatus, so as to allow engagement thereof in an analyzer.

According to still further features in the described preferred embodiments the at least one reaction vessel is disposable.

According to still further features in the described preferred embodiments the at least one reaction vessel includes a plurality of reaction vessels.

According to still further features in the described preferred embodiments the at least one reaction vessel includes a plurality of reaction vessels arranged in an array.

According to still further features in the described preferred embodiments the array is an m by n array, wherein m and n are integers each independently selected from the group consisting of 1, 8, 12, 16, 24 and 32 and their multiplication by an integer greater than 1.

According to still further features in the described preferred embodiments the apparatus further comprising a spectrometer being in optical communication with the distal end of the at least one reaction vessel such that the optical properties of the at least one liquid reaction mixture can be monitored while contained within the at least one reaction vessel.

According to still further features in the described preferred embodiments the temperature controller includes a timing mechanism which serves for determining a time period limitation for at least one temperature setting.

According to still further features in the described preferred embodiments the apparatus further comprising a user interface, being in electrical communication with the temperature controller, the user interface being for selecting a sequence of temperature settings including at least two distinct temperatures each selectable for a predetermined time period.

According to still further features in the described preferred embodiments the at least one liquid reaction mixture is selected from the group consisting of a DNA polymerase reaction mixture, a reverse transcription reaction mixture, a ligation reaction mixture, and a nuclease reaction mixture.

According to still further features in the described preferred embodiments the DNA polymerase reaction mixture is a PCR reaction mixture. According to yet another aspect of the present invention there is provided a system for performing and analyzing at least one biological or chemical reaction, the system comprising (a) an apparatus for executing the at least one biological or chemical reaction in at least one liquid reaction mixture, including (i) at least one reaction vessel having open proximal and distal ends, the at least one reaction vessel including a gas permeable, liquid retaining barrier positioned at a proximal portion thereof; (ii) a pump being in fluid communication with the proximal end of the at least one reaction vessel through the barrier and for generating negative or positive pressure within the at least one reaction vessel for translocating the at least one liquid reaction mixture, through the distal end, into and out of the at least one reaction vessel; and (iii) a temperature controller being in thermal communication with the at least one reaction vessel for controlling the temperature of the at least one liquid reaction mixture when maintained within the at least one reaction vessel; and (b) an analyzer including (i) at least one container being for receiving the at least one liquid reaction mixture following execution of the at least one biological or chemical reaction; and (ii) a mechanism for analyzing the at least one liquid reaction mixture.

According to still further features in the described preferred embodiments the analyzer is selected from the group consisting of a chromatographic column, an electrophoretic device, a spectrophotometer, a scintillation counter, a fluorometer.

According to still further features in the described preferred embodiments the at least one container of the analyzer is in fluid communication with the at least one reaction vessel of the apparatus for executing the at least one biological or chemical reaction.

According to still further features in the described preferred embodiments the at least one container forms a part of a multititer plate and the mechanism for analyzing is a multititer plate reader.

The present invention successfully addresses the shortcomings of the presently known configurations by providing an apparatus system and method for executing and analyzing a biological and chemical reaction.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
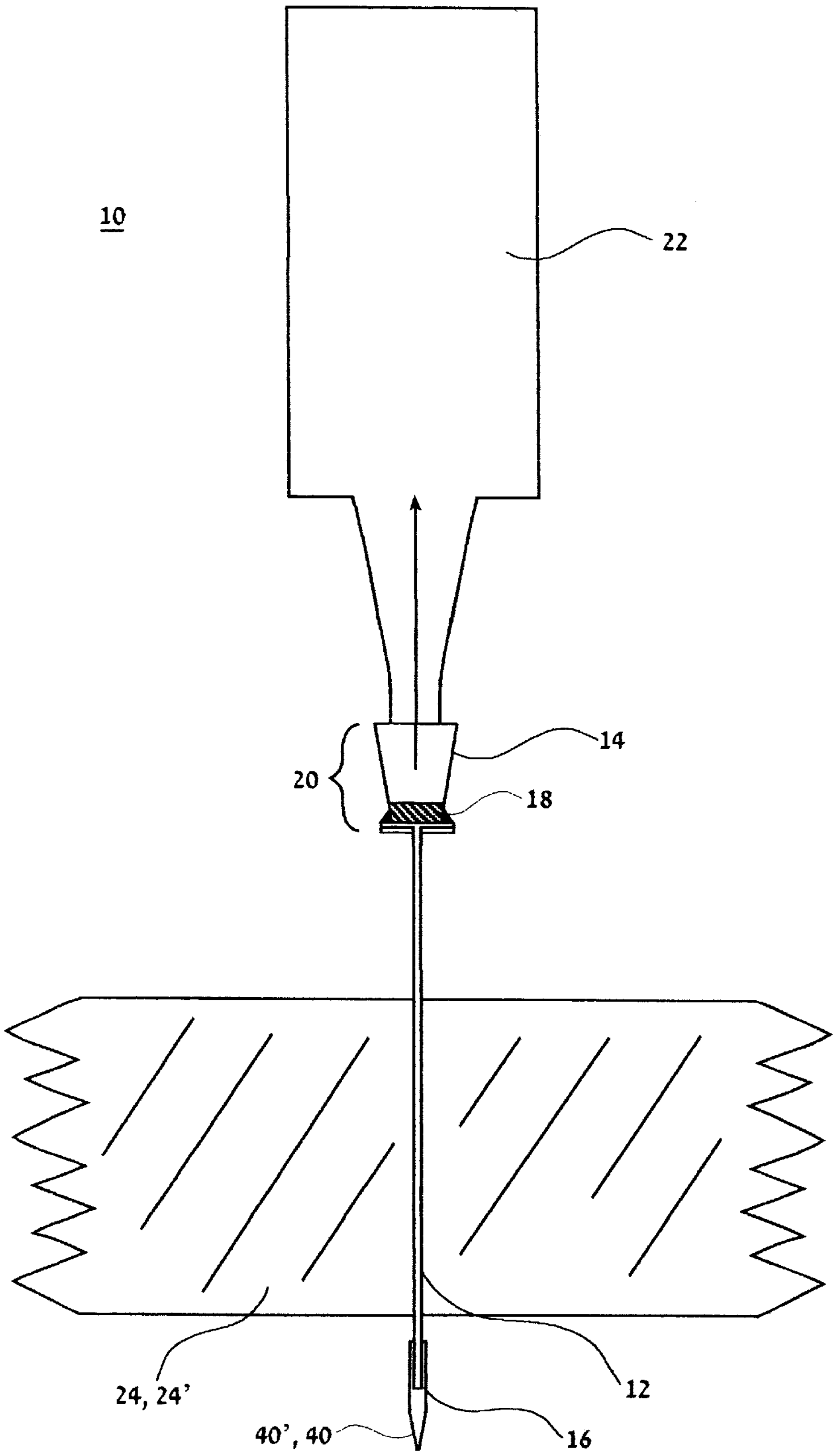
FIG. 1 is a cross sectional view of one configuration of an apparatus for controlling the temperature of a liquid reaction mixture according to the present invention.

The present invention is of an apparatus, system and method which can be utilized for executing and analyzing biological and chemical reactions automatically. Specifically, the present invention can be used to automate nucleic acid reactions, such as, for example, the polymerase chain reaction (PCR) and sequencing, thus allowing automatic reaction product analysis either during, or immediately following, a nucleic acid reaction.

The principles and operation of an apparatus, system and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being. practiced or carried out in various ways. Also, it is to be understood that the phraseology and terminology employed herein is for the purpose of description and should not be regarded as limiting.

Figure 2:
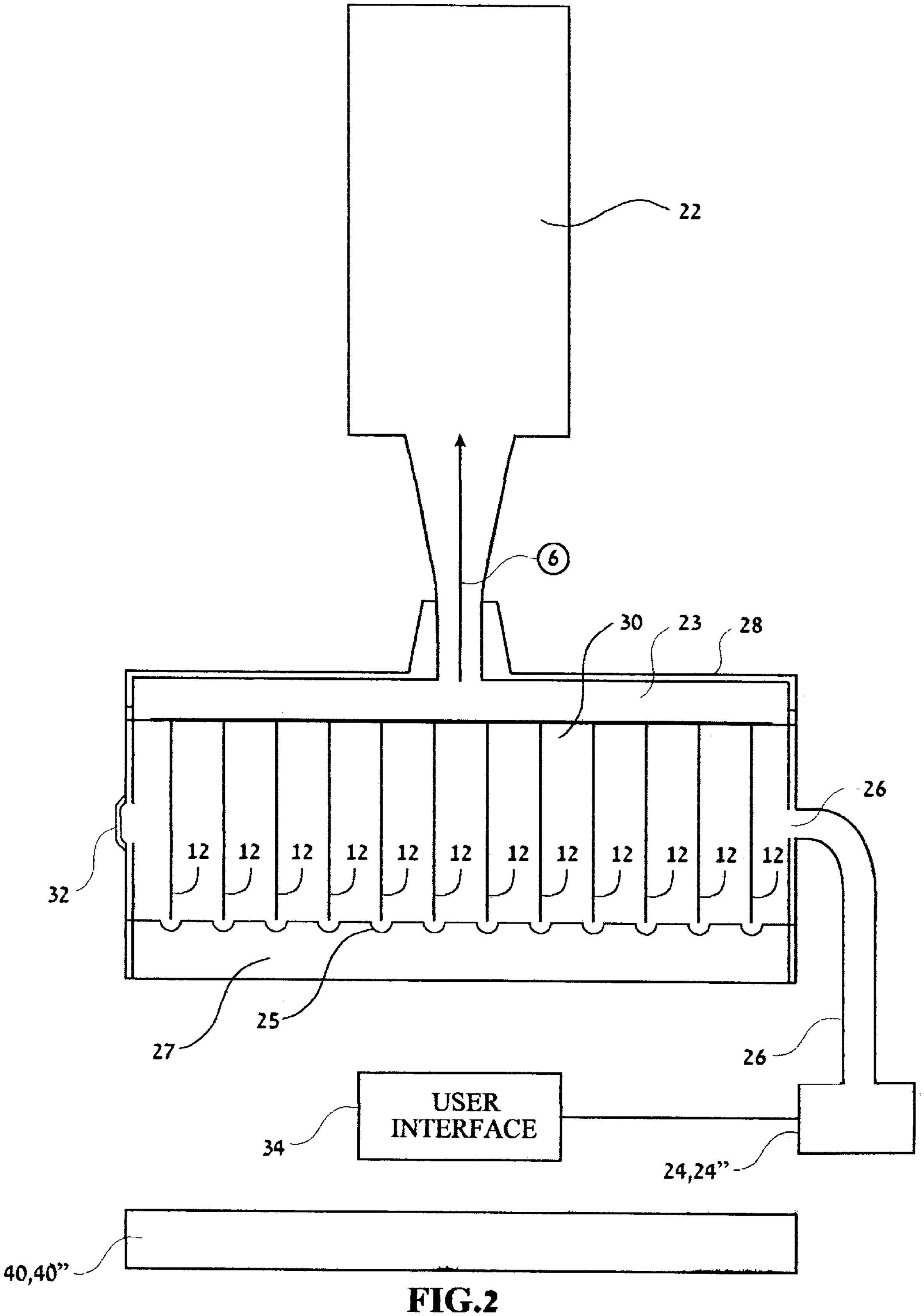
FIG. 2 is a cross sectional view of another configuration of an apparatus for controlling the temperature of a liquid reaction mixture according to the present invention.
Figure 3:
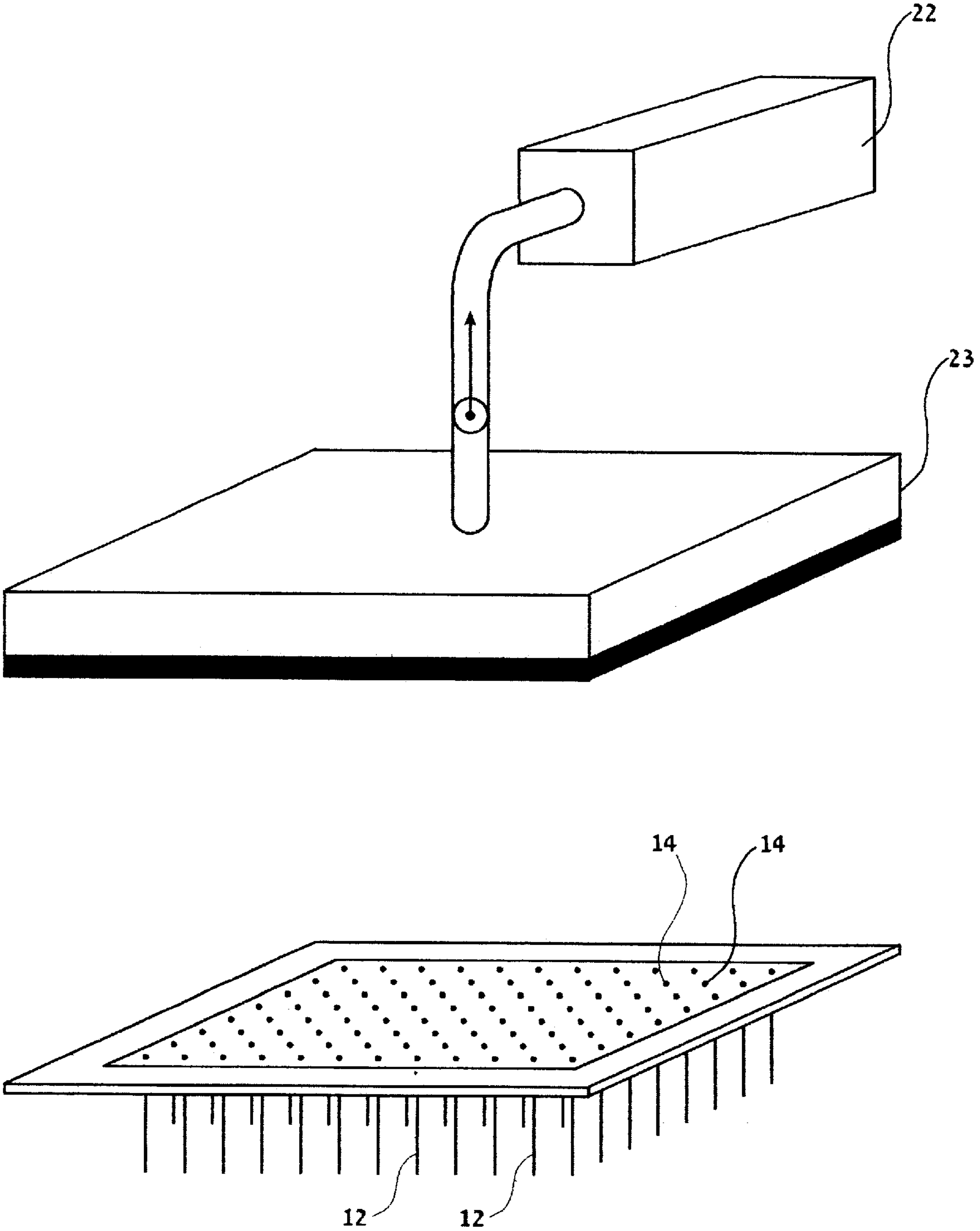
FIG. 3 is a perspective view of an apparatus for controlling the temperature of a liquid reaction mixture according to the present invention.

Referring now to the drawings, FIGS. 1–3 illustrate an apparatus in accordance with the teachings of the present invention which is referred to hereinbelow as apparatus 10.

As seen in FIG. 1, apparatus 10 includes a vessel 12 having open proximal 14 and distal 16 ends. Vessel 12 is preferably formed of a material with good thermal conductivity properties, such as, but not limited to, glass, compound material, semiconductor material, certain heat conducting plastics and in particular metal. Vessel 12 is preferably disposable and as such is replaced following the execution and/or analysis of a reaction therein, so as to avoid cross-contamination. As shown in FIGS. 2 and 3, apparatus 10 preferably includes a plurality of vessels 12, which can be arranged in an array of m by n vessels, wherein m and n are integers, such as, but not limited to, 1, 8, 12, 16, 24 and 32, and any multiplication thereof by an integer greater than 1. Presently preferred configurations include arrays of 1×10, 1×12, 1×8 and 8×12. Vessel 12 is preferably tubular or needle like having a length ranging between 3 and 100 mm, preferably, between 5 and 70 mm, more preferably between 10 and 50 mm, most preferably, between 20 and 30 mm; an inner diameter ranging between 0.2 and 3 mm, preferably, between 0.3 and 2 mm, more preferably between 0.5 and 1 mm, most preferably, between 0.7 and 0.9 mm; a wall thickness ranging between 0.03 and 1 mm, preferably, between 0.05 and 0.5 mm, more preferably between 0.07 and 0.3 mm, most preferably, between 0.1 and 0.2 mm; and a volume ranging between 0.09 and 706 $\mu t$, preferably, between 0.35 and 219 $\mu l$, more preferably between 2 and 39 $\mu l$, most preferably, between 7 and 19 $\mu l$.

Vessel 12 includes a gas permeable, liquid retaining barrier 18 which is positioned at a proximal portion 20 thereof. The terms "barrier", "filter" and "membrane" are used herein interchangeably.

Barrier 18 is preferably designed such that it is permeable to air or gas but at the same time, substantially impermeable to liquids and molecules contained therein.

As used herein in the specification and in the claims below, a "gas permeable" barrier includes all barriers which are permeable or partially permeable to at least one gas, a mixture of gases, or a portion of a mixture of gases.

As used herein in the specification and in the claims section that follows, the phrase "liquid retaining" refers to complete or partial impermeability to at least one liquid and as a result, liquid complete or partial retainability, under conditions employed.

Barrier 18 is preferably composed of a hydrophobic material, such that hydrophilic liquids such as water and molecules participating in biological or aqueous based chemical reactions, which are largely hydrophilic are retained by barrier 18.

Barrier 18 is preferably selected to function as herein described within a temperature range of zero ° C., zero–4° C., or zero–10° C. at the lower temperature end, and up to 90° C., 90–94° C. or preferably 90–100° C. at the upper temperature end.

Membranes or filters which can be utilized as a barrier by apparatus 10 of the present invention are preferably hydrophobic filters or membranes, such as those made of a fluorocarbon polymer (TEFLON), an example of which includes a polytetrafluoroethylene (PTFE) filter, distributed, for example, by Whatman Inc., Japan Millipore Ltd., Gelman Sciences Inc. or by W.L. Gore & Associates Inc. Another example of a hydrophobic filter is a filter made of polyvinylidene fluoride (PVDF), such as the DURAPORE (hydrophobic PVDF) produced by Millipore Inc. Additional examples include filters which are hydrophilic and coated by a hydrophobic coat, such as silanized or siliconized filters.

Barrier 18 is preferably selected to retain at least 99%, preferably, at least 99.5%, more preferably, at least 99.9%, more preferably at least, 99.99%, most preferably, at least 99.999% of particles larger than 0.5, preferably 0.25, more preferably 0.1, still more preferably 0.05, most preferably 0.01 $\mu$m in diameter.

As specifically shown in FIG. 3, a single sheet of membrane or filter can serve to form a plurality of barriers 18 to a plurality of vessels 12 arranged in an array. In this case, the single sheet is preferably glued or welded over a platform which receives the proximal ends of vessels 12, so as to seal the proximal ends of vessels 12. However, such sealing can also be effected by a perforated platform which is pressed against the platform which receives the proximal ends of vessels 12. In the latter case, pump 22 communicates with vessels 12 via the perforations of the perforated platform.

Apparatus 10 further includes a pump 22 which is in fluid communication with proximal end 14 of vessel 12 (as shown in FIG. 1) or a plurality of vessels 12 (as shown in FIGS. 2–3). Should apparatus 10 include a plurality of vessels 12, an adapter 23 is preferably provided, through which fluid communication between proximal ends 14 of vessels 12 and pump 22 is established. Pump 22 serves to draw and eject the liquid reaction mixture(s) into and out of vessel(s) 12 as so required. While withdrawing the liquid reaction(s) into vessel(s) 12 via pump 22, barrier 18 serves as a blockade to limit the volume of the liquid reaction(s) withdrawn into vessel(s) 12.

Since fluid communication between vessel(s) 12 and pump 22 is provided through barrier 18, substantially only air or gas, and to a much lesser extent water as vapor, is translocated to and from vessel(s) 12 via pump 22. As such, pump 22 serves for generating negative or positive pressure within vessel(s) 12, such that a liquid reaction mixture can be translocated through distal end into and out of vessel(s) 12.

Apparatus 10 further includes a temperature controller 24 which is in thermal communication with vessel(s) 12. Temperature controller 24 serves for heating and cooling the reaction mixture(s) contained within vessel(s) 12 to a temperature typically selected from the range of 0–100° C. Preferably, temperature controller 24 is configured such that cooling or heating of the reaction mixture(s) is effected rapidly. Preferably, temperature controller 24 generates a temperature increase or decrease of 10° C. within the liquid reaction mixture(s) within 0.1–10 seconds, more preferably within 0.2–5 seconds, most preferably within 0.5–1 seconds. To provide accurate temperature settings, temperature controller 24 is preferably in communication with a temperature sensor or probe (not shown). The temperature sensor or probe serves to provide temperature controller 24 with the actual or calculated temperature of the liquid reaction mixture(s). As well known in the art, algorithms for temperature management which take into account vessel volume, reaction volume and other parameters can and are preferably employed while practicing the present invention.

According to a preferred embodiment of the present invention and as seen in FIG. 1, temperature controller 24 includes a thermal block 24' which is designed for accepting in intimate thermal contact, vessel 12 or any number of vessels 12. Heating and cooling of thermal block 24' can be effected via the Peltier effect, via water of preset temperatures or via any other cooling and heating mechanisms and methods which are known and/or which are commonly used in the art.

According to another preferred embodiment of the present invention and as seen in FIG. 2 temperature controller 24 includes an air-based thermal cycler 24" which serves for providing a temperature controlled air stream to vessel(s) 12 through a fluid connection 26. It will be appreciated that for an air-based thermal cycler to be effective, vessel(s) 12 must be enclosed within a housing. Thus, as seen in FIG. 2, apparatus 10 also includes a housing 28 for enclosing vessels 12 in a thermal chamber 30. It will be appreciated that in order to enable rapid temperature changes within thermal chamber 30, rapid air substitution must be effected within chamber 30. To this effect, housing 28 is preferably provided with an openable gate 32 through which air contained within chamber 30 can be rapidly evacuated and replaced by another air stream of a distinct temperature which is provided from temperature controller 24. It will be appreciated that other thermal cyclers such as water based thermal cyclers can also be utilized by temperature controller 24 of apparatus 10 of the present invention.

To set the temperature provided by temperature controller 24, apparatus 10 further includes a user interface 34 which is in electrical communication with controller 24. Interface 34 can be used to set a desired temperature for a desired time period, or any number of sequential or cyclic, time period dependent, temperature setting s.

Thus according to the present invention apparatus 10 can be utilized to control the temperature of liquid reaction mixture(s) contained within vessel(s) 12. Such a liquid reaction mixture can include components for a biological or chemical reaction, which reaction is executed by providing a specific temperature setting for a predefined time period or alternatively a specific sequence which includes various temperature and time settings.

According to a preferred embodiment of the present invention and as further detailed in Example 1 below, apparatus 10 is used for executing a PCR reaction.

Thus, to execute the biological or chemical reaction the liquid reaction mixture is drawn via pump 22 through distal end(s) 16 of vessel(s) 12. The liquid reaction mixture is preferably drawn from liquid reaction mixture reservoirs 25 (FIG. 2) arranged in an array 27. The liquid reaction mixture is then retained in vessel(s) 12 by one of several means which are further described hereinunder. Thereafter, temperature controller 24 is operated via user interface 34 to provide a time dependent temperature setting or a sequence of temperature settings in order to execute the reaction.

According to another preferred embodiment of the present invention the liquid reaction mixture is retained within vessel(s) 12 via a removable seal 40.

As used herein in the specification and in the claims section that follows, the phrase "removable seal" refers to a seal formed at an end of a vessel 12 which can be removed non-destructively and resealed multiple times if necessary without damaging vessel 12. Seal 40 can be constructed of any formable sealing material, such as, but not limited to, rubber, silicone, plastic and the like, which is configured to provide a close fluid tight fit with distal end(s) 16. As specifically shown in FIG. 1, removable seal 40 can be constructed as a removable cap 40' so as to seal a single vessel 12, or preferably, as shown in FIG. 2, as a sealing surface 40", which when in use replaces array 27. Alternatively, distal end 16 of each of vessels 12 can be placed in a reservoir of liquid, preferably oil, that is not miscible with the liquid reaction mixture. Seal 40 provides a fluid tight barrier thus preventing the liquid reaction mixture or vapors derived therefrom from escaping vessel(s) 12. According to a preferred embodiment of the present invention, when seal 40 is utilized to retain the liquid reaction mixture within vessel(s) 12, atmospheric pressure or a positive pressure, between 20 and 100 torr, is applied to the liquid reaction mixture from pump 22 such that formation of water vapor which can form, for example, when the liquid reaction mixture is heated, is minimized. The positive pressure is preferably selected high enough so as to maintain a positive pressure within vessel(s) 12 under all temperatures employed. In a preferred embodiment, the operation of pump 22 is controlled so as to maintain a constant positive pressure value, regardless of the temperature.

It will however be appreciated that the use of a distally applied seal 40 generates a limitation. Scaling the distal end of reaction vessel 12 negates the possibility of inserting an optical probe therein for real-time analysis during the course of reaction.

Therefore, according to another and presently preferred embodiment of the present invention the liquid reaction mixture is contained within vessel(s) 12 by generating a negative pressure within vessel(s) 12 via pump 22. Thus, according to this configuration following drawing the liquid reaction mixture(s) into vessel(s) 12 a negative pressure, e.g., 20–40, preferably about 30 millitorr, is maintained within vessel(s) 12 so as to contain the liquid reaction mixture(s) therein. The negative pressure is selected low enough so as to maintain a negative pressure within vessel(s) 12 under all temperatures employed. In a preferred embodiment, the operation of pump 22 is controlled so as to maintain a constant negative pressure value, regardless of the temperature.

It will be appreciated that barrier 18 included within proximal portion 20 of vessel(s) 12 serves in this case for preventing the liquid reaction mixture from being drawn into, and thereby contaminating, pump 22.

The use of negative pressure for containing the liquid reaction mixture is particularly advantageous since distal end 16 remains unoccluded and as such the liquid reaction mixture is easily amenable to real time analysis during the course of the reaction as is further described hereinbelow.

Apparatus 10 according to the present invention provides a distinctive advantage over prior art designs in that it employs, in combination, open reaction vessels arranged in an array and a barrier at a proximal end thereof. As such, apparatus 10 according to the present invention is not prone to nucleic acid contamination, as is the device disclosed in U.S. Pat. No. 5,897,842, while, at the same time, enjoys some advantages of that device in terms of subsequent analysis, i.e., the ability to easily further process the reactions without being required to handle each vessel individually. An apparent advantage of apparatus 10 of the present invention over the teaching of U.S. Pat. No. 5,897,842 is evident when negative pressure is employed to retain the reaction mixtures within the vessels. Such a design obviates the need for a removable seal, which, as further detailed hereinunder, renders the reaction amenable to real-time monitoring. It will be appreciated that since apparatus 10 of the present invention employs open reaction vessels preferably arranged in an array, it can automatically draw preprepared liquid reaction mixtures from any automated sample preparation device, examples of which are mentioned hereinabove in the Background section above. Such sample preparation devices can also be employed post reaction to prepare the reactions for subsequent analysis. In addition, and as further detailed hereinunder, an analyzer can be integrated with apparatus 10 to thereby provide a partially or fully automated system for both executing and concomitantly or subsequently analyzing or monitoring the reactions.

Figure 4:
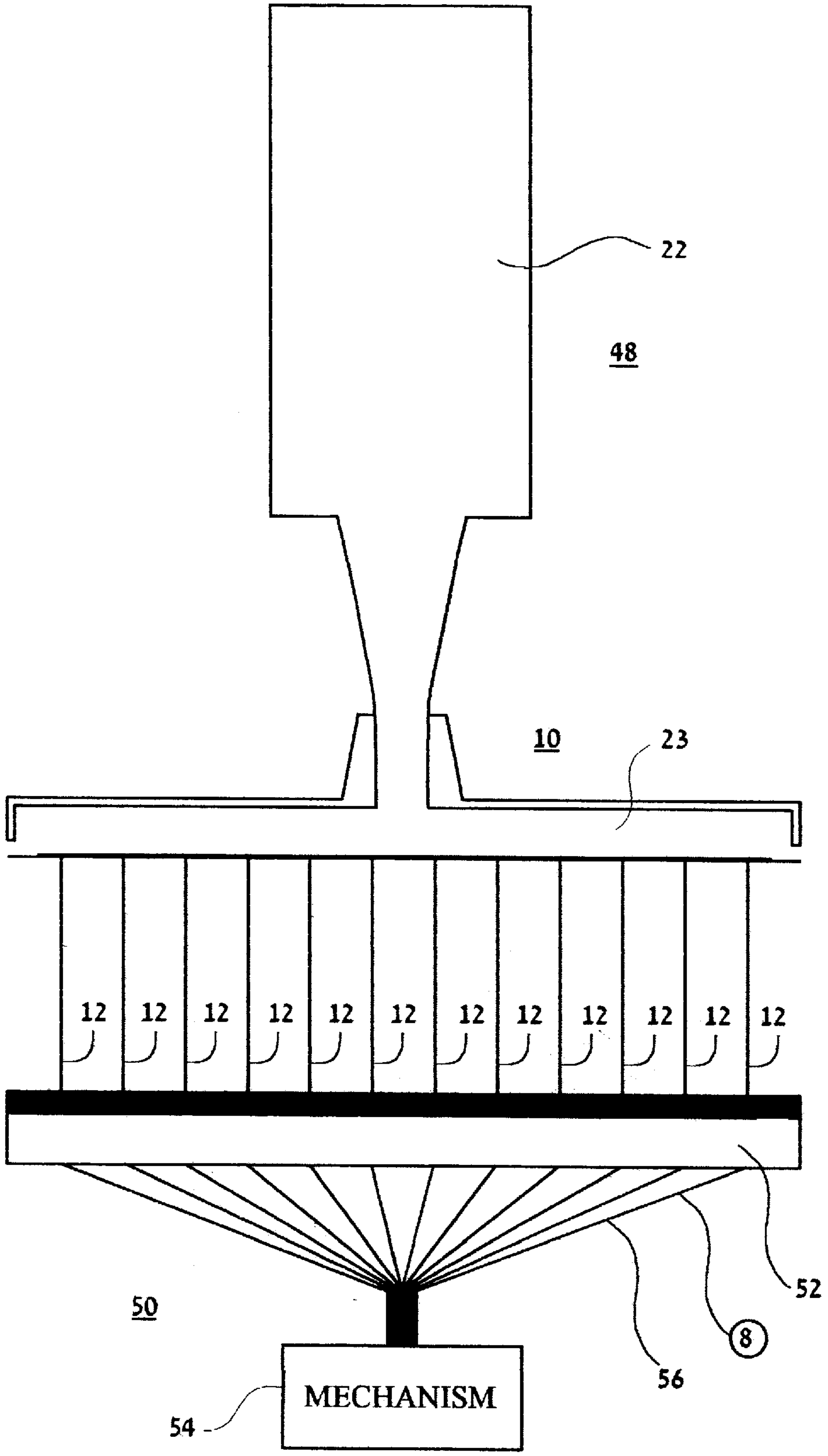
FIG. 4 is a schematic depiction of a system for executing and analyzing a reaction in a liquid reaction mixture according to the present invention.

Thus, as shown in FIG. 4, according to another aspect of the present invention apparatus 10 forms a part of a system for executing and analyzing a biological or chemical reaction, which is referred to hereinbelow as system 48.

In addition to apparatus 10, system 48 further includes an analyzer 50. Analyzer 50 serves for analyzing the liquid reaction mixture(s) contained within vessel(s) 12 either concomitantly with their propagation or subsequent to their termination. Analyzer 50 includes an adapter 52 interfacing with distal end(s) 16 of vessel(s) 12. Adapter 52 can, for example, include a container or an array of containers co-alignable with vessel(s) 12. The container(s) serve for receiving at least a portion of the liquid reaction mixture(s) either during, or following the completion, of the reaction (s), such that specific analysis can be performed thereon. The liquid reaction mixture(s) or sample(s) therefrom can be ejected from vessel 12 by temporarily reversing the negative pressure applied from pump 22, such that a controllable and selectable volume of the liquid reaction mixture is provided to the container(s).

Analyzer 50 further includes a mechanism 54 for analyzing the liquid reaction mixture(s). Analyzer 50 is in communication with adapter 52 via electrical, fluid or optical lines 56 depending on the configuration of analyzer 50 utilized. Several analytical processes can be employed by the analyzer of the present invention depending on the configuration of adapter 52. Analysis can be performed chemically (for example, reaction with marker molecules) chromatographically (for example, gel electrophoresis) or electrically (for example electrical conductivity of the reaction mixture) each designed for the detection of specific products formed or depleted during the course of the reaction.

According to a preferred embodiment of the present invention, adapter 52 is an optical adapter and as such mechanism 54 is a spectrometer for measuring optical density, fluorescence or any other optical property of the liquid reaction mixture(s).

As used herein in the specification and the claims section that follows, the term "spectrometer" includes any optical device capable of monitoring light modulation. To this end, a spectrometer includes a light source and one or more light detectors. It may additionally include filters, reflectors, lenses, prisms, interferometers, beam splitters, light-guides and the like optical components.

Figure 5A:
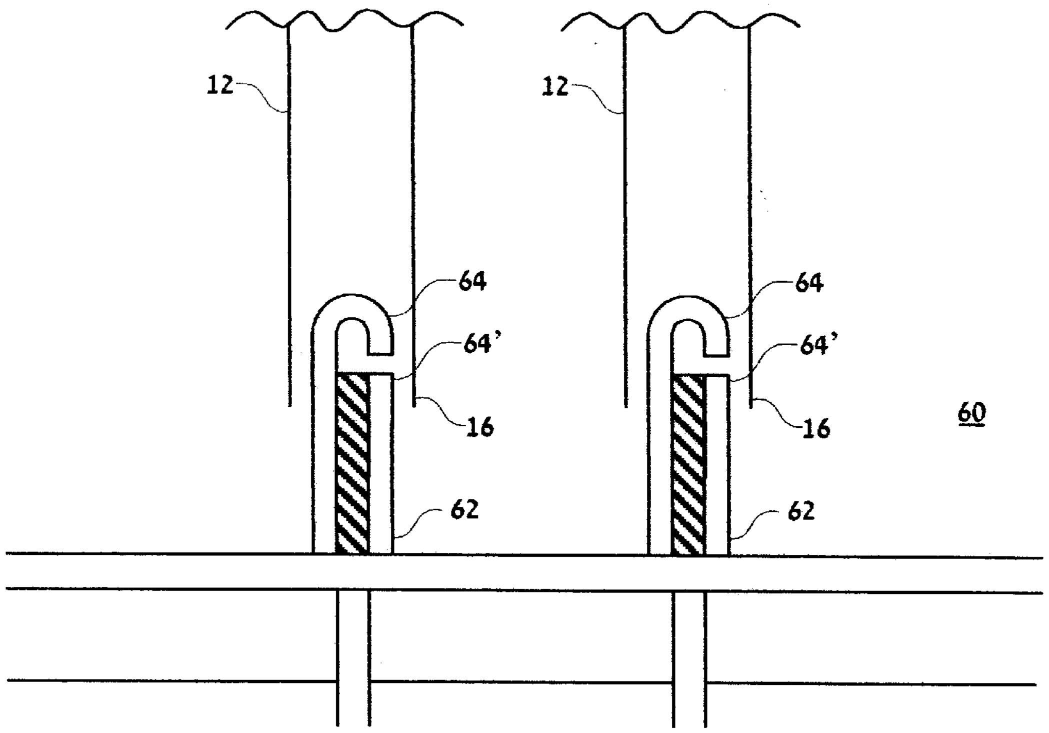
FIG. 5*a* is a cross sectional view of one configuration of an optical interface of an analyzer according to the present invention.
Figure 5B:
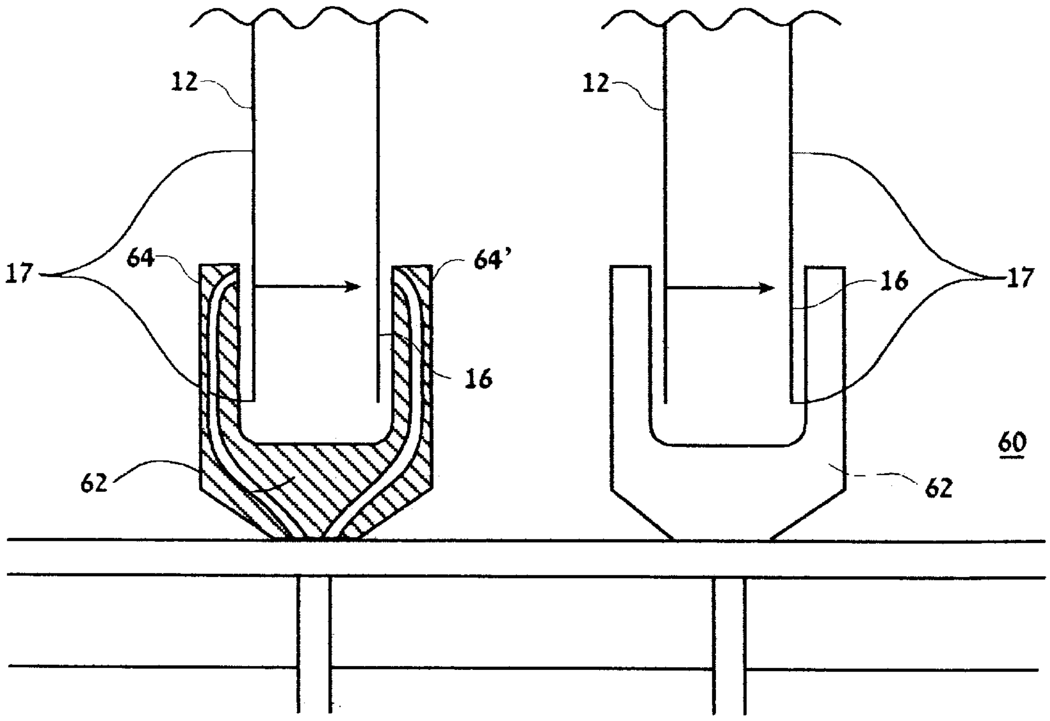
FIG. 5*b* is a cross sectional view of another configuration of an optical interface of an analyzer according to the present invention.
Figure 5C:
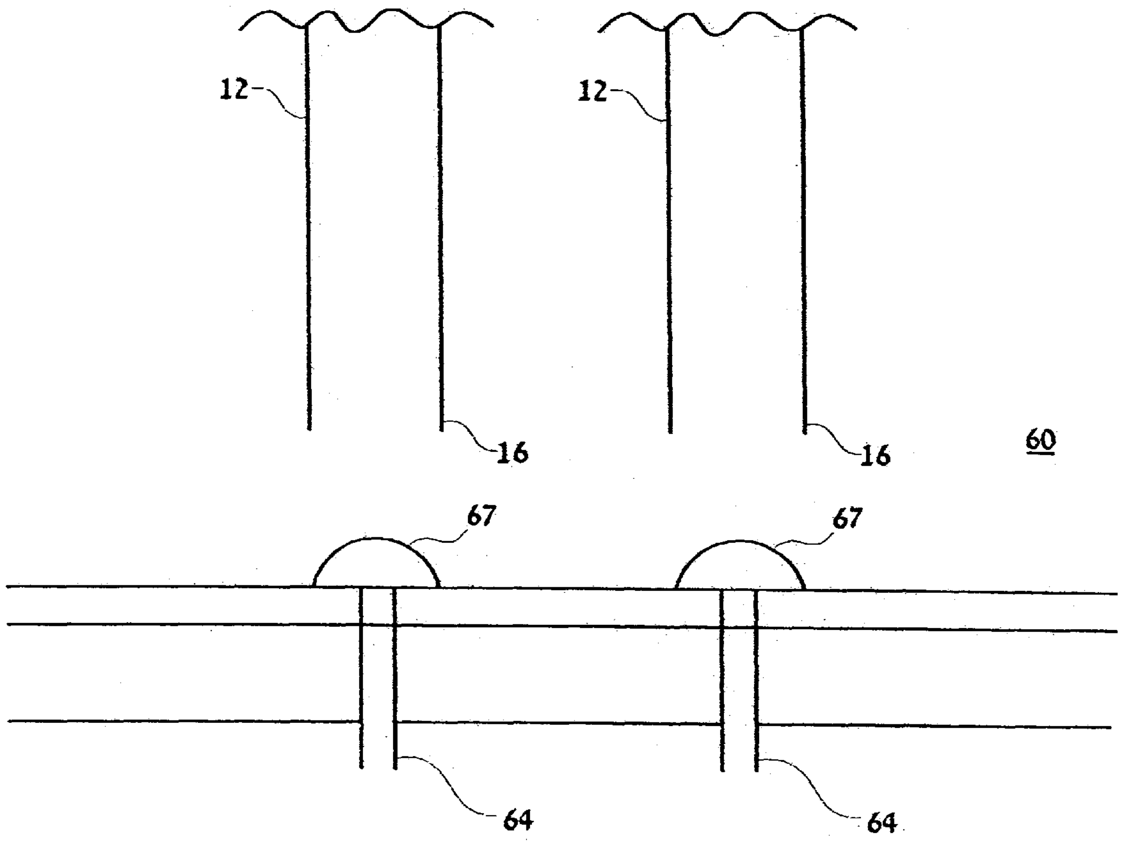
FIG. 5*c* is a cross sectional view of yet another configuration of an optical interface of an analyzer according to the present invention.

As such, and as specifically shown in FIGS. 5*a–c* the adapter (52 in FIG. 4) includes an optical interface 60 which is in optical communication with liquid reaction mixtures through distal ends 16, such that an optical analysis can be performed on any liquid reaction mixture during its execution or following its termination. As seen in FIG. 5*a*, optical interface 60 includes optical probe(s) 62 insertable into distal end(s) 16 of vessel(s) 12. Each of optical probes 62 includes a single or a pair of light guides 64 and 64', e.g., optical fibers. Following insertion of a probe 62 into a distal end 16 of a vessel 12, a light beam produced from a light source is propagated by first light guide 64 or the single light guide. The beam then traverses or is reflected from the liquid reaction mixture and is subsequently picked up by second light guide 64' which is positioned opposite to first light guide 64, or the single light guide, to thereby deliver light to a light detector and thereby monitor light modulation associated with the progression of the reaction in the liquid reaction mixture.

The specific wavelengths employed depend to a large extent on the type of reaction. One ordinarily skilled in the art would know how to select wavelengths which can provide useful information relating to the propagation of a given reaction.

For example, the incorporation of nucleoside-triphosphates into a DNA molecule is associated with an increase in absorbance of short wave ultraviolet radiation. It is further associated with fluorescence of intercalating agents such as, but not limited to, ethidium bromide. Therefore, either ultraviolet light modulation or ultraviolet or visible light induced fluorescence can be monitored by illuminating the liquid reaction mixture with ultraviolet or visible light by a light guide and further by monitoring light modulation or induced fluorescence via the same or an additional light guide and a light detector.

Alternatively and as shown by FIG. 5*b* probe 62 provides a pair of light guides 64 and 64' arranged in an opposing orientation, positioned outside a distal portion 17 of vessel 12. It will be appreciated that for this configuration to be operable, vessel 12 or at least distal portion 17 thereof must be of a substantially transparent material allowing transmittance of a light beam provided by light guide 64 through liquid reaction mixture to be picked up by light guide 64'.

In both of the above mentioned optical configurations the optical properties of the liquid reaction mixture are then analyzed by mechanism 54 which harbors the light source and the light detector which are, as. already mentioned above, in optical communication with light guides 64 and 64'. It will be appreciated that a light beam can be transmitted through or emitted from the liquid reaction mixture by other means employing lenses, beam splitters and the like.

Still alternatively, in the configuration shown in FIG. 5*c*, a single light guide 65 serves to remotely illuminate the reaction mixture(s) through distal end(s) 16 of vessel(s) 12 through a focusing lens 67. Fluorescence is concomitantly collected by lens 67 and propagated via light guide 65 to a light detector for analysis.

Figure 6:
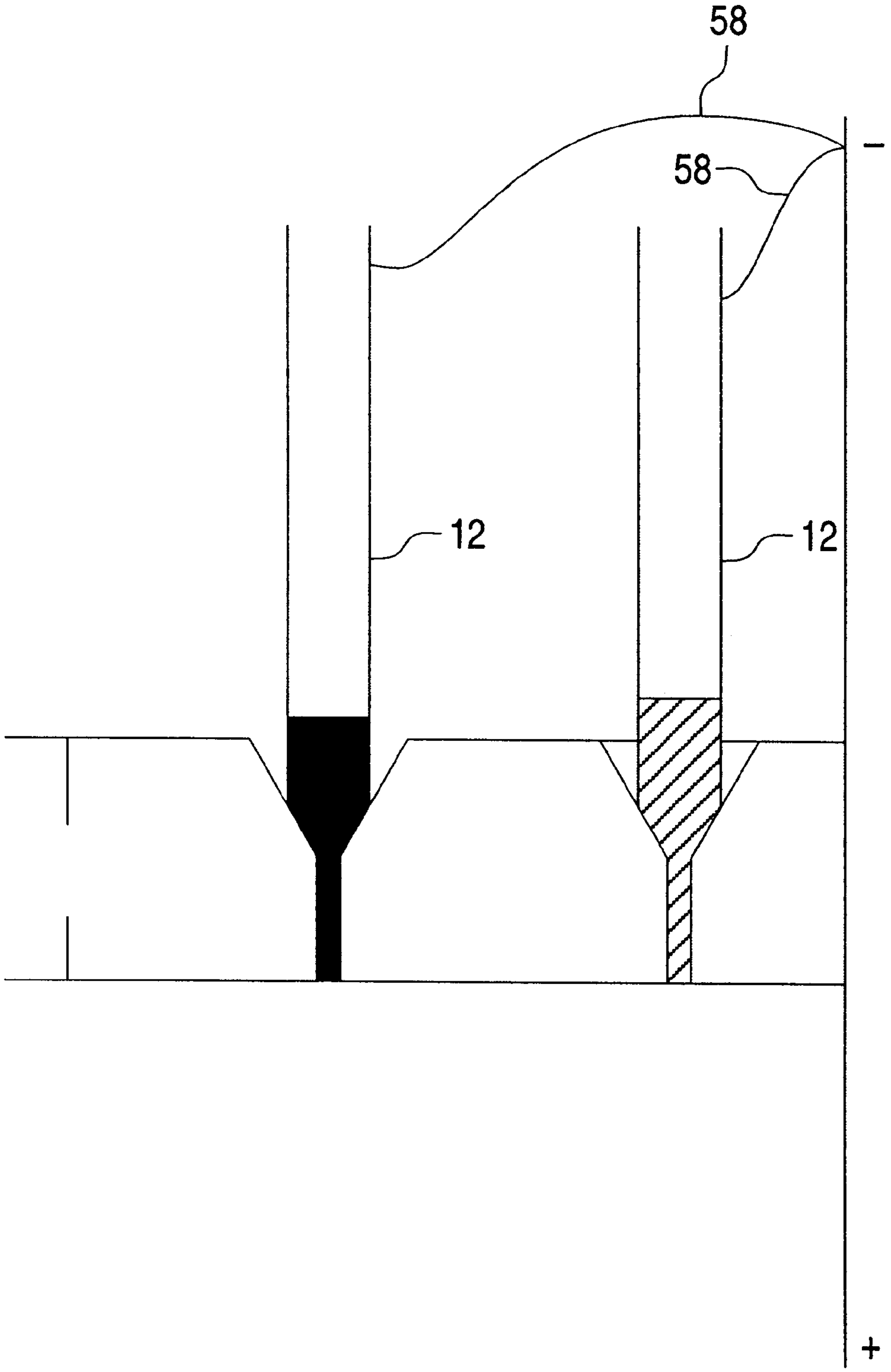
FIG. 6 is a schematic depiction of a reaction vessel as utilized in gel or capillary electrophoresis following the execution of a reaction therein according to the present invention.

According to another preferred embodiment of the present invention, and as seen in FIG. 6, vessel 12 can be detached from apparatus 10 following the reaction and be introduced into a gel electrophoresis device, such as, but not limited to, a capillary gel electrophoresis device including, for example, agarose or acrylamide gel. In this case, vessel 12 is preferably composed of an electrically conductive material such that it can be used directly in electrophoresis by providing distal end 16 thereof into a loading well of an electrophoretic device and electrically connecting, as indicated at 58, vessel 12 to one electrode end of the electrophoretic device.

According to a preferred embodiment of the present invention, system 48 is utilized for executing and analyzing biological reactions such as, but not limited to, DNA polymerase reactions, reverse transcription reactions, ligation reactions, and nuclease reactions.

According to another preferred embodiment of the present invention system 48 is utilized for amplifying DNA sequences and analyzing the amplified products. These products can be analyzed by analyzer 50 to detect specific nucleic acid sequences and sequence changes. As used hereinunder the term “sample” and the phrase “liquid reaction mixture” are used interchangeably.

Amplification of target nucleic acid sequences can be provided via several methods which typically rely on the PCR method. PCR enables a repeated replication of a desired specific nucleic acid sequence using two oligonucleotide primers complementary each to either strand of the sequence to be amplified. Extension products, to which these primers are incorporated, then become templates for subsequent replication steps. The method selectively increases the concentration of a desired nucleic acid sequence in a geometric rate even when that sequence is not purified prior to amplification, and is present only in a single copy in a particular sample. The PCR method may be used to amplify either single or double-stranded DNA or complementary DNA (cDNA).

In addition to amplification methods, additional methods are known in the art which may be used to detect and characterize specific nucleic acid sequences and sequence changes. Like PCR, these methods can be executed and analyzed by the present invention and as such be provided on a large scale in a fast, reliable, and cost-effective manner. These methods include sequencing and cycled sequencing, allele specific amplification and ligase chain reaction (LCR).

In addition, methods of post reaction analysis of nucleic acid products include, but are not limited to, allele specific oligonucleotide (ASO) hybridization; reverse-ASO; denaturing/temperature gradient gel electrophoresis (D/TGGE); single-strand conformation polymorphism (SSCP); heteroduplex analysis; restriction fragment length polymorphism (RFLP); nuclease protection assays; chemical cleavage and other, less frequently used, methods. Each of these reactions can be performed by a dedicated analyzer subsequent to the termination of the reaction simply by ejecting via the pump the content of the vessels or samples therefrom into a multititer plate, treating the samples as required and analyzing the results, obviating the need to open each vessel independently.

Thus, the present invention provides a rapid, accurate, cost effective and easily operable apparatus and system with which a large number of reactions can be simultaneously executed and their products analyzed even in real time. As such, the present invention is particularly advantageous for performing various diagnostic tests in which the ability to simultaneous execute and analyze a large number of reactions provides advantages including reducing costs and shortening diagnosis times. In addition, because the apparatus and system according to the present invention can be rendered fully automated, the accuracy thereof, which is of vital importance in diagnostics, is greatly increased over prior art designs, especially those which rely heavily on human operators.

One main advantage of the present invention over prior art designs is that it employs open vessels which are, as already mentioned, amenable for real-time monitoring.

Additional objects, advantages, and novel features of the present invention will become apparent to one ordinarily skilled in the art upon examination of the following example, which is not intended to be limiting.

EXAMPLE

Reference is now made to the following example, which together with the above descriptions, illustrate the invention in a non limiting fashion.

A reaction vessel made of stainless steel was fabricated by modifying a hypodermic needle (G18, Becton & Dickerson) as follows.

The sharp distal end of the needle was trimmed and pinched. inwardly, but the needle was left open. A hydrophobic filter (0.2 $\mu$m pore size PTFE filter), was glued to the bottom of the needle's plastic housing, which is attached to the proximal end of the needle. The hydrophobic filter employed serves according to the present invention as a barrier for aqueous solutions, including the liquid reaction mixture. A one ml syringe (Pronto Siringa Gliss, Como, Italy) was utilized for drawing approximately 15 $\mu$l of a PCR reaction mixture into the needle.

The PCR reaction mixture included: 10 mM Tris-HCl, pH 8.3, 50 mM KCl, 3 mM $MgCl_2$, 0.001% gelatin (modified, ×2 $MgCl_2$ of Sigma P2192 PCR buffer), deoxynucleotides mix 0.2 mM (Sigma D7295), BSA 5 mg/ml (Sigma A2153, added just before the enzyme), Taq DNA Polymerase 0.05 units/$\mu$l (Sigma D 6677), circular plasmid DNA pBarnase 0.5 ng/$\mu$l as template and 0.2 $\mu$M of each primer (T7-5'-GTAATACGACTCACTATAGGGC-3' (SEQ ID NO:1) and 675-5'-CTAGCTAGCAGTGAAATTGACCGATCAGAG-3' (SEQ ID NO:2)) designed to amplify a 447 bp PCR product.

By continuing to pull the syringe piston to 1 ml, a vacuum was produced above the filter. The vacuum was maintained during thermal cycling by locking the piston in a fully extended position.

The reaction vessel was placed in a commercial air-heated cycler (RapidCycler, Id.) in the original, or in a modified adapter, in place of one of the glass capillaries, and a three step temperature cycle was executed according to the following settings of the thermo-cycling program: 15 seconds at 94° C.; 30 cycles of 94° C., 0 seconds (i.e., no delay prior to next temperature), 50° C., 0 seconds, and 72° C., 15 seconds; followed by 30 seconds at 72° C. Following the termination of the PCR reaction, the liquid reaction mixture was ejected via the syringe into a microfuge tube, mixed with a loading dye and loaded onto a 1% TAE agarose/EtBr gel.

Figure 7:
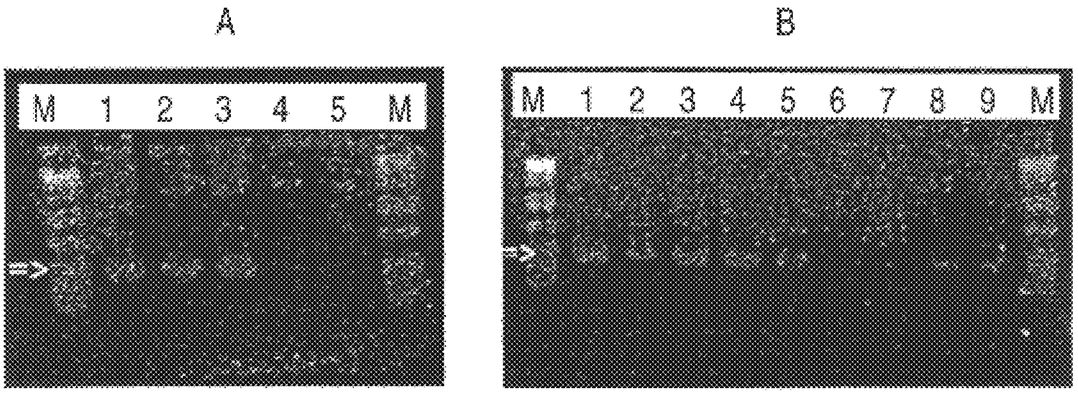
FIG. 7 is a photograph of polymerase chain reaction amplification products amplified using the apparatus of the present invention, separated on an agarose gel, stained with ethidium bromide and photographed under ultraviolet illumination.

FIG. 7B shows a 447 base pair fragment amplified by the above procedure (lanes 1–5), or in sealed glass capillaries which were used as positive controls (lanes 8 and 9).

It should be noted that using the 0.2 $\mu$m pore size PTFE filter with negative pressure, as described above, resulted in some water vapor and as a consequence small water droplets accumulating above the filter. This causes a loss of up to 20% of the volume of the reaction mixture. Nevertheless, as is clearly seen in FIG. 7B, such volume losses did not affect the amplification results. The drops accumulated above the filters of 5 individual syringes were collected (approximately 15 $\mu$l) and separated on an agarose gel. The existence of DNA was not detected in this combined sample (FIG. 7B, lane 6).

In addition, DNA was not detected when thermocycling was not effected (FIG. 7A, lanes 4 and 5, and 7B lane 7).

In an additional experiment, the reaction mixture was drawn via a syringe following which the blunted needle tip was covered with a plastic cap. The syringe piston was then compressed to produce a positive pressure within the reaction vessel. Thereafter the vessel was placed in the air-heated cycler and PCR was effected as above. The electrophoresis results show a similar 447 base pair DNA band (FIG. 7A, lanes 1–3). This time no appreciable volume losses from the liquid reaction mixture were detected.

It will be appreciated that although some water loss through the barrier was experienced while using the negative pressure method, no appreciable loss of DNA or reduced efficiency of amplification was experienced by this method. On the contrary, results in terms of quantity of amplified product were superior to those obtained using the capillary vessels. This could be explained by the improved heat transfer and, as a result, temperature homogeneity of metal as is compared to glass. As is clearly seen in FIG. 7 both the positive (FIG. 7*a*) and negative (FIG. 7*b*) pressure methods produce similar results in amplifying a 447 base pair DNA fragment.

In a subsequent experiment a 0.1 $\mu$m pore size PTFE filter (GORE TEX, W.L. Gore & Associates Inc.) was used instead of the 0.2 $\mu$m pore size PTFE filter described above, while keeping all other parameters identical. Using the 0.1 $\mu$m pore size PTFE filter, PCR yields were identical however, no appreciable water loss was experienced when vacuum was employed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

---

What is claimed is:

1. An apparatus for controlling the temperature of at least one liquid reaction mixture, the apparatus comprising:

(a) at least one reaction vessel having open proximal and distal ends, said at least one reaction vessel including a gas permeable, liquid retaining, barrier being positioned at a proximal portion thereof, (b) a pump being in fluid communication with said proximal end of said at least one reaction vessel through said barrier, for generating negative or positive pressure within said at least one reaction vessel, for translocating the at least one liquid reaction mixture through said distal end into and out of said at least one reaction vessel, wherein the at least one liquid reaction mixture is retained within said at least one reaction vessel via said negative pressure generated therein by said pulp, thereby obviating a need of sealing said distal end; and (c) a temperature controller being in thermal communication with said at least one reaction vessel for controlling the temperature of the at least one liquid reaction mixture when maintained within said at least one reaction vessel.

2. The apparatus of claim 1, further comprising a removable seal positionable at said distal end of said at least one reaction vessel, said removable seal being for restricting the at least one liquid reaction mixture within said at least one reaction vessel when sealed.

3. The apparatus of claim 1, wherein said temperature controller is a thermocycler capable of cycling at least two temperature settings.

4. The apparatus of claim 1, wherein said temperature controller includes a thermal block designed for accepting in intimate thermal contact said at least one reaction vessel.

5. The apparatus of claim 4, wherein said thermal block forms a part of a thermocycler capable of cycling at least two temperature settings.

6. The apparatus of claim 1, further comprising a housing for enclosing said at least one reaction vessel, wherein said temperature controller is an air-based thermal cycler, for providing a temperature controllable air stream into said housing.

7. The apparatus of claim 1, wherein said at least one reaction vessel is of a material selected from the group consisting of glass, compound material, semiconductor material, plastic and metal.

8. The apparatus of claim 1, wherein said at least one reaction vessel is composed of a heat conducting material.

9. The apparatus of claim 1, wherein said at least one reaction vessel is composed of an electricity conducting material.

10. The apparatus of claim 1, wherein said at least one reaction vessel is removable from the apparatus, so as to allow engagement thereof in an analyzer.

11. The apparatus of claim 1, wherein said at least one reaction vessel is disposable.

12. The apparatus of claim 1, wherein said at least one reaction vessel includes a plurality of reaction vessels.

13. The apparatus of claim 1, wherein said at least one reaction vessel includes a plurality of reaction vessels arranged in an array.

14. The apparatus of claim 1, wherein said array is an m by n array, wherein m and n are integers each independently selected from the group consisting of 1, 8, 12, 16, 24 and 32 and their multiplication by an integer greater than 1.

15. The apparatus of claim 1, further comprising a spectrometer being in optical communication with said distal end of said at least one reaction vessel such that the optical properties of the at least one liquid reaction mixture can be monitored while contained within said at least one reaction vessel.

16. The apparatus of claim 1, wherein said temperature controller includes a timing mechanism which serves for determining a time period limitation for at least one temperature setting.

17. The apparatus of claim 1, further comprising a user interface, being in electrical communication with said temperature controller, said user interface being for selecting a sequence of temperature settings including at least two distinct temperatures each selectable for a predetermined time period.

18. A system for performing and analyzing at least one biological or chemical reaction, the system comprising:

(a) an apparatus for executing the at least one biological or chemical reaction in at least one liquid reaction mixture including:

(i) at least one reaction vessel having open proximal and distal ends, said at least one reaction vessel including a gas permeable, liquid retaining barrier being positioned at a proximal portion thereof;

(ii) a pump being in fluid communication with said proximal end of said at least one reaction vessel through said barrier and for generating negative or positive pressure within said at least one reaction vessel for translocating the at least one liquid reaction mixture, through said distal end, into and out of said at least one reaction vessel, wherein the at least one liquid reaction mixture is retained within said at least one reaction vessel via said negative pressure generated therein by said pump, thereby obviating a need of sealing said distal end; and (iii) a temperature controller being in thermal communication with said it least one react ion vessel for controlling the temperature of the at least one liquid reaction mixture when maintained within said at least one reaction vessel; and (b) an analyzer including:

(i) at least one container being for receiving said at least one liquid reaction mixture following execution of the at least one biological or chemical reaction; and (ii) a mechanism for analyzing said at least one liquid reaction mixture.

19. The system of claim 15, wherein said analyzer is selected from the group consisting of a chromatographic column, an electrophoretic device, a spectrophotometer, a scintillation counter and a fluorometer.

20. The system of claim 18, wherein said at least one container of said analyzer is in fluid communication with said at least one reaction vessel of said apparatus for executing the at least one biological or chemical reaction.

21. The system of claim 19, wherein said at least one container forms a part of a multititer plate and said mechanism for analyzing is a multititer plate reader.

22. A method of controlling the temperature of at least one liquid reaction mixture, the method comprising the steps of:

(a) providing at least one reaction vessel having open proximal and distal ends, said reaction vessel including a gas permeable, liquid retaining barrier positioned at a proximal portion thereof;

(b) drawing the at least one liquid reaction mixture into said at least one reaction vessel from said distal end;

(c) retaining the at least one liquid reaction mixture within said at least one reaction vessel by applying negative pressure from said proximal end of said at least one reaction vessel, thereby obviating a need of sealing said distal end; and (c) setting a temperature of the at least one liquid reaction mixture contained within said at least one reaction vessel via a temperature controller.

23. The method of claim 22, wherein said at least one liquid reaction mixture is selected from the group consisting of a DNA polymerase reaction mixture, a reverse transcription reaction mixture, a ligation reaction mixture, and a nuclease reaction mixture.

24. The method of claim 23, wherein said DNA polymerase reaction mixture is a PCR reaction mixture.

* * * * *

UNITED STATES PATENT AND TRADEMARK OFFICE
CERTIFICATE OF CORRECTION

PATENT NO. : 6,200,781 B1
DATED : March 13, 2001
INVENTOR(S) : Tal et al.

It is certified that error appears in the above-identified patent and that said Letters Patent is hereby corrected as shown below:

Column 2,
Line 62, change "either" to -- neither --
Line 64, change "his" to -- this --

Column 3,
Line 29, change "thereof," to -- thereof; --
Line 46, change "scaled" to -- sealed --

Column 6,
Line 48, change "μt," to -- μl, --

Column 8,
Line 46, change "setting s." to -- settings. --

Column 9,
Line 34, change "Scaling" to -- Sealing --

Column 13,
Line 17, after "pinched" delete -- . --
Line 42, change "Id." to -- Idaho --

Column 15,
Line 27, change "thereof," to -- thereof; --
Line 37, change "pulp" to -- pump --

Column 17,
Line 8, change "react ion" to -- reaction --

Signed and Sealed this

Second Day of April, 2002

*Attest:*

JAMES E. ROGAN

*Attesting Officer* *Director of the United States Patent and Trademark Office*